United States Patent
Renault et al.

[11] Patent Number: 6,155,101
[45] Date of Patent: Dec. 5, 2000

[54] METHOD AND DEVICE FOR PREPARING A FUEL, PARTICULARLY FOR DIESEL ENGINES, BY ON-LINE MIXTURE OF ITS COMPONENTS

[75] Inventors: Francois Renault, Le Havre; Daniel Lebreton, Le Pecq; Jean-Pierre Drouault; Alain Picart, both of Saint Laurent deBrevedent, all of France

[73] Assignee: Total Raffinage Distribution S.A., Puteaux, France

[21] Appl. No.: 09/171,235

[22] PCT Filed: Apr. 9, 1997

[86] PCT No.: PCT/FR97/00627

§ 371 Date: Feb. 25, 1999

§ 102(e) Date: Feb. 25, 1999

[87] PCT Pub. No.: WO97/39349

PCT Pub. Date: Oct. 23, 1997

[30] Foreign Application Priority Data

Apr. 15, 1996 [FR] France ................................. 95 04656

[51] Int. Cl.[7] ................................................. G01N 33/22
[52] U.S. Cl. ................................ 73/35.2; 44/903; 123/304
[58] Field of Search ..................... 73/35.02; 123/304; 44/903

[56] References Cited

U.S. PATENT DOCUMENTS

| | | |
|---|---|---|
| 3,469,954 | 9/1969 | Hoffman . |
| 3,520,173 | 7/1970 | Hadley . |
| 3,575,039 | 4/1971 | Beal ........................................ 73/35.02 |
| 3,672,840 | 6/1972 | Fenske et al. ........................... 73/35.02 |
| 3,913,380 | 10/1975 | Jones et al. ............................ 73/35.02 |
| 3,949,595 | 4/1976 | Jones et al. ............................ 73/35.02 |
| 4,010,358 | 3/1977 | Morris ..................................... 73/35.02 |
| 4,331,024 | 5/1982 | Childs et al. ........................... 73/35.02 |
| 4,402,212 | 9/1983 | Childs .................................... 73/35.02 |
| 5,457,985 | 10/1995 | Cellier et al. .......................... 73/35.02 |
| 5,633,798 | 5/1997 | Kopp ..................................... 73/35.02 |
| 5,906,190 | 5/1999 | Hole et al. .............................. 73/35.02 |
| 6,026,778 | 2/2000 | Mille et al. ............................. 73/35.02 |

FOREIGN PATENT DOCUMENTS

| | | |
|---|---|---|
| 610 118 | 8/1994 | European Pat. Off. . |
| 1 270 838 | 11/1962 | Germany . |

OTHER PUBLICATIONS

Derwent Pub. JP 63 139 988, Jun. 1988, Abstract.
"On–Line Octane Measurement and Its Influence on Blending Plant Design and Operation" by Jones et al, pp 19–23, vol. 3, No. 1, Jan. 1970 Measurement and Control.

*Primary Examiner*—Erick Solis
*Attorney, Agent, or Firm*—Sughrue, Mion, Zinn, Macpeak & Seas, PLLC

[57] ABSTRACT

A C.F.R. engine (26) is alternately supplied with a fuel being manufactured (22), sampled from the discharge line of the mixer and, through a line (24), with a reference product (25) of which the cetane number is known, by two separate supply circuits (22, 24) each having a high pressure fuel pump (33, 34), the C.F.R. engine (26) operating at a constant compression ratio.

17 Claims, 2 Drawing Sheets

METHOD AND DEVICE FOR PREPARING A FUEL, PARTICULARLY FOR DIESEL ENGINES, BY ON-LINE MIXTURE OF ITS COMPONENTS

FIELD OF THE INVENTION

This invention relates to a method and apparatus for the preparation of a fuel, and particularly a fuel for diesel motors, or a fuel for heating systems, by mixing its constituents in line, and possibly incorporating additives.

BACKGROUND OF THE INVENTION

The fuels for diesel motors are designed to auto-ignite after being injected in highly compressed air. They generally consist of a mixture of various constituents in proportions such that the fuel has certain qualities and meets certain related specifications, for example, cold resistance, sulfur content and value of cetane.

In the refining plants, such a fuel is obtained through a technique called in line mixing, by which the various liquid constituents, as well as additives, are introduced simultaneously and continuously in one duct serving as a mixer. The flow rate of the various constituents is controlled and operated by computer and the preparation time of one batch of fuel can take up to 30 hours.

Naturally, the properties of the resulting product are monitored several times during the making and analyses are completed on samples taken from the outflow of the mixer, or from the: storage tank during the filling. From the results of theses analyses, the flow rates of the mixture's, constituents and of the additives are adjusted to align the measured values with the set values.

Of course, for each analysis, there is an advantage to limiting as much as possible the time periods between the time when the sample of the mixture during preparation was taken and the time the measured value was obtained, and, in general, the analyzers used for this procedure, called in line analyzers, meet this requirement.

However, one of the most important properties of diesel motors fuels, namely their capacity to auto ignite, is not submitted to an on line control as it exits the mixer because of the difficulties involved in measuring this characteristic. It is defined as the time between the injection of fuel and its ignition in a combustion chamber, under conditions set by the ASTM D 613 standards, where the unit of measurement is conventionally called the cetane number.

According to the conditions of measurement, the value 15 of this cetane number is attributed, to heptamethylnonane, whereas the value 100 corresponds to the combustion under the same conditions of normal cetane (normal hexadecane). An intermediary $\underline{CN}$ number (Cetane Number, attributed to a fuel means that the latter has an auto ignition equal to that of a mixture of heptamethylnonane and normal cetane such that:

$$CN = x + 0.15(100 - x)$$

where x is the cetane content (% per volume) of the heptamethylnonane and normal cetane mixture.

The measuring, long and complicated, takes place in very precise conditions set by the ASTM D 613 standard, with the help of a device defined in the same standard. This device contains a diesel motor adjusted by the Corporation Fuel Research company and universally known in the field under the name of "C.F.R. motor". However, the measurement procedure with this device is lengthy (approximately 1 hour), delicate and requires many manual interventions.

Methods and apparatuses have been perfected in order to reduce the measuring time while still automatically generating the measurement in question. In particular, the application for European patent EP-A-0 610 118, which relates to the procedure as described in the SAE 890419 document, proposes a method and apparatus for continuously measuring the cetane index. If these methods anti apparatuses enhance the method for measuring a fuel's cetane, they nevertheless have some drawbacks, such as the use of common circuits and capacities for the standard product and the fuel sample during manufacturing, as well as the need to use many electrovalves with their pilot systems, There are other methods for measuring the auto ignition delay of a fuel, such as the calculation of the cetane number from easily measured properties, such as density or distillation characteristics. However, the results obtained are not very reliable and do not take into account the frequent introduction in certain types of fuel of a procetane additive designed to increase, if necessary, the cetane number of the mixture. It is interesting to note, along these lines, that the CFI motor does in fact take the effect of the procetane additive into account in its measurements.

There is therefore a need, in this technique for a fast, reliable and automatic measurement system, used in line during the preparation procedure of a fuel for diesel motors, that allows to better control the auto ignition characteristic represented by the cetane number.

DISCLOSURE OF THE INVENTION

This is the problem that this invention intends to solve, by using an in line CFR type apparatus, downstream of the mixer and under conditions such that the results of the cetane number measurement can be easily known very shortly after having taken the test sample.

The invention also aims to propose an in line mixing method and apparatus for the constituents, and possibly for the additives, of a fuel for diesel motors, where the measurement of the cetane number of the mixture is fast, reliable and completely automated.

With this end in view, the objective of this invention is a method for preparing a fuel, in particular for diesel motors, or a fuel for heating systems, through an in line mixing of its constituents with the possible introduction of additives, and, since this fuel will be marketed, it should. have a specific cetane number; the method consists of continuously feeding a mixer with the various constituents at controlled flows, measuring, at the output of the mixer and at different time periods, the cetane number of the fuel being prepared, calculating the difference between the measured values and the set values, this method is characterized by the fact that during manufacturing a "CFR" motor is alternately fed a fuel, taken from the mixer's exhaust line, then a standard product with a known cetane number, through two separate fuel systems each comprised of a high pressure injection pump, and where the CFR motor is operating at a constant compression ratio.

The calculation of the cetane number of the sample to be measured as compared to the already known cetane number of the standard product, will be easy completed by applying the terms of the ASTM D 2885 standard for the in line analyzer part, a standard that is already used to determine the octane number of gasoline. In practice, the ignition delay of a sample of the mixture being manufactured and the ignition delay of a standard product with a known cetane number are measured sequentially, under the same conditions and with a same CFR motor. These measurements done on the fuel during manufacturing and then on the standard product, take less than one hour, and even less than ten minutes.

For each series of measurements, the cetane number of the mixture sample being manufactured will be determined based on information provided in the form of electrical signals by the CFR motor (auto-ignition delays of the sample, the mixture and the standard product), this information is then converted, by means of a calculator, in differences of cetane as compared to the standard product, the calculator will then complete the calculation of the cetane number of the sample to be measured in terms of the known cetane number of the standard product.

This sample cetane number will then be transmitted to a computer programmed to pilot the related quantities of the different constituents introduced in the mixer.

In accordance with the ASTM D 2885 standard, the precision of the measurement of the cetane number by the apparatus consistent with the invention is directly tied to the precision of the cetane number of the standard product, this precision is generally equal to or lesser than 1 cetane point for a standard product having been measured several times and whose average value is equal to 50. Advantageously, when compared to the precision of the method described in the ASTM D 613 standard, the precision of the cetane number measurement by the apparatus in accordance with the invention is therefore enhanced by a factor that can vary between two and five.

Note that in the invention's method, the CFR motor is used at a constant compression ratio and, therefore, under conditions that are different from those of the ASTM D 613 standard this: recommend a variable compression ratio and involve a comparison between two perfectly defined sample products with cetane numbers respectively higher and lower that of the sample. The use or the CFR motor with a constant compression ratio avoids having to resort to mechanical drive movements during the measurements and is therefore favorable to an automation of the measuring procedure and thus to an enhancement of the measurements precision.

The sample product used will have a cetane number close to that being sought for the mixture being manufactured, and where the difference with the set value is less than 5 cetane points and preferably less than 2.

The mixture sample and the sample product that feed the CFR motor are introduced through separate circuits in the same injection area of such motor; this will avoid having to purge between the two successive measurements, and therefore allow for a reduction in the stabilization time of such measurements. These two measurements (mixture sample and standard product) can be done in any order.

Each CFR motor feed circuit will be equipped with a separate high pressure injection pump, this is an important advantage of the method introduced by the invention as it will avoid the use of controlled systems for example to trigger the opening and closing of the electrovalves, execute intermediary adjustments between the measurements on a single pump, or trigger the rinsing of the aforementioned pump when the standard product flows through to the fuel in the process of being manufactured. Only one preadjustment is necessary for both systems prior to implementing the; procedure for a manufacturing cycle.

The measuring system will therefore be easy to automate since it will only be necessary to alternately control one pump of one or the other feed circuits of the CFR motor.

An in line addition, in adjustable quantities, of a procetane additive in the mixer, or upstream or downstream of the mixer, can be done, as with the previous technique, but, as indicated above, the measurements taken by the CFR device take this procetane into account, this is an important advantage of the method of this invention.

The purpose of the invention is also an apparatus for manufacturing a fuel, in particular a fuel for a diesel motor, or a fuel for heating systems, by mixing its constituents in line with the possible incorporation of additives, and, since it will be marketed, this fuel must have a specific cetane number; this apparatus will consist of at least two tanks for stocking at least two constituents of the mixture, a mixer fed by separate lines with adjustable flows of various constituents of the mixture, at least one exhaust line for the mixture prepared in the mixer, preferably a tank for storing the manufactured product, possibly a source of procetane additives with adjustable and automated flow, connected downstream or upstream to the mixer and/or the exhaust line, a means of measuring the cetane number, at least one means of controlling the debit of various feeding lines of the mixer and the procetane feed circuit, with this means of control being on the one hand, controlled through comparisons and on the other hand, programmed so as to adjust the different flows in order to reduce the gaps between the measured values and the set cetane number values, this device being characterized by the fact that:

the means of measurement intended to measure the cetane number of the mixture consists of a CFR type motor, preferably shunt connected to the exhaust line of the mixer.

this CFR motor is respectively connected by lines equipped with a controlled means of closure, to the aforementioned exhaust line and to a source of a standard product with a. known cetane number.

the CFR motor is pre-adjusted to operate at constant compression ratios and with arm advance to the adjusted injection at a predetermined value.

the CFR motor is equipped to provide, by controlling the flows from different feed lines of the mixture's constituents, or possibly of an additive, a signal that represents the difference, between the two measurements of the cetane number, such measurements being taken successively from the mixture and from the standard product or vice versa.

As indicated above, the feed lines of the CFR motor for the mixture sample to be tested and the product with the known cetane number will preferably be separate or will only have a small common section, and each will be equipped with an injection pump. Non-return valves can obviously be provided for on the feed lines of the CFR motor.

Preferably, the injection pumps will be piloted by an automatic control able to activate them at regular intervals set ahead of time, for example every five minutes.

A known fact in itself, the CFR motor's injection pumps for the mixture sample and the standard product will consist of two adjustment systems, one for the quantity to be injected, the other for the time of injection, and both these systems will be able to be adjusted independently.

The CFR motor will preferably be calibrated by two standard fuels with cetane numbers close to that of the sample product.

The attached diagrams illustrate the implementation of the invention. On these drawings, only the measurement and adjustment systems of the cetane number have been represented, and not the systems of a known type used either to calibrate a measuring device or to measure and adjust other preset properties of the fuel. On these diagrams:

Figure 1:
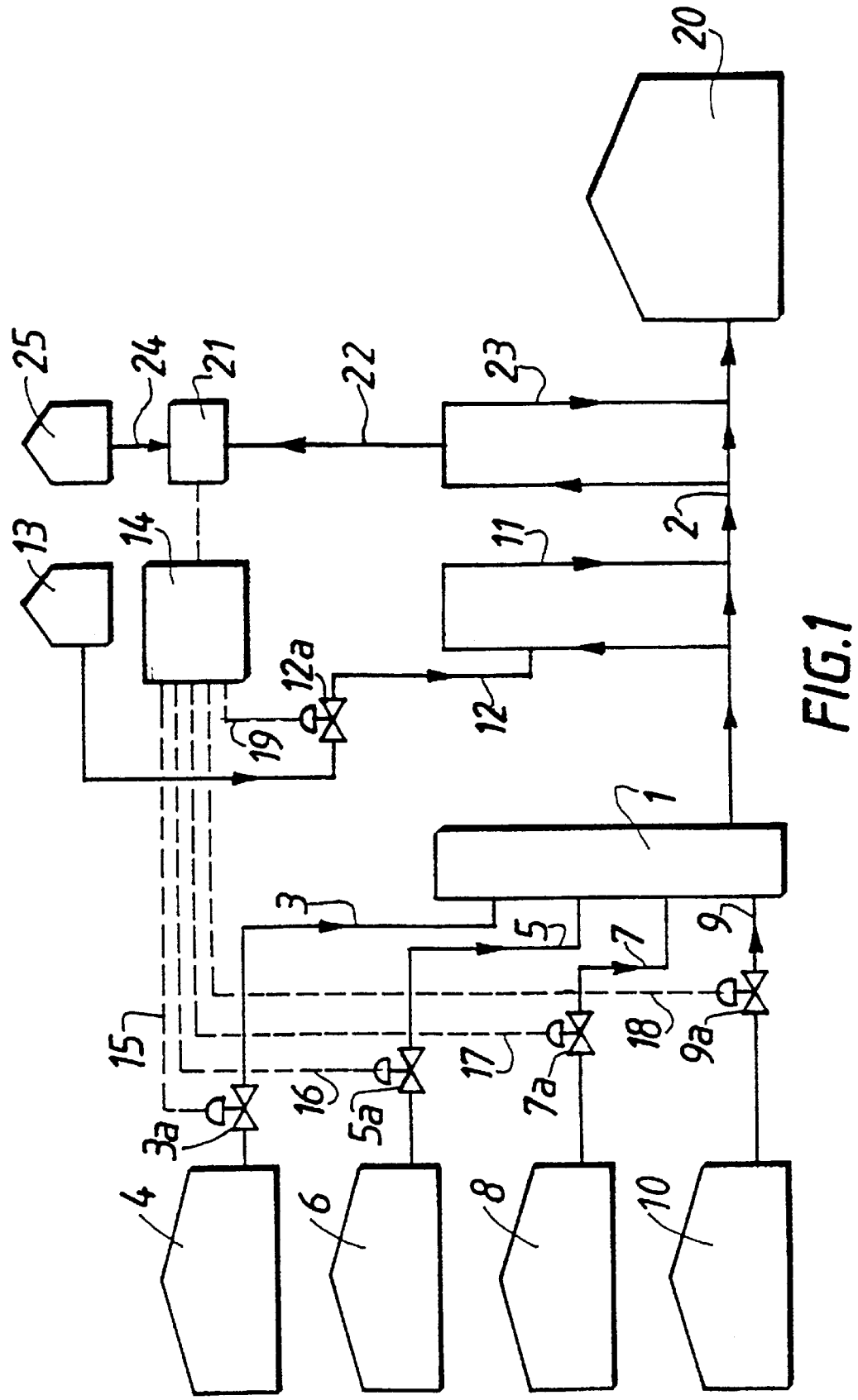
FIG. 1 is a drawing of the entire in line mixing apparatus for the fuel constituents.

The apparatus represented in FIG. 1 is designed to create a gas oil that has predetermined properties and in particular a preset cetane number, by mixing various constituents in line in a mixer 1 and, potentially in the exhaust line 2 of this mixture toward a tank 20. In this case, the mixer I is fed various constituents of the mixture, emanating from the storage tanks (4, 6, 8, 10) through four lines (3, 5, 7, 9) each equipped with a valve that automatically adjusts the flow (3a, 5a, 7a, 9a) These various constituents, of which one must have a cetane number of a lesser value than that of the set value, can for example be, without however being limited thereto, a heavy gas resulting from a catalytic cracker, a light fraction resulting from a crude oil distillation column, a gas oil with a high sulfur content, or a gas oil with a low sulfur content resulting from a gas oil desulfurization unit.

In a loop circuit 11, shunt connected to the exhaust line 2, an additive called procetane such as, for example, 2-ethyl-hexyl-nitrate, can be injected through a line 12, equipped with an automatic flow adjustment valve 12a, from a tank 13.

As explained above, various in line analyzers (not represented) are connected in a known fashion to line 2 downstream of the procetane injection, in order to periodically measure the characteristic properties of the mixture and compare the measured values with the set values of these properties. These analyzers are connected to a computer 14, which is connected by lines 15, 16, 17, 18 and 19 to valves 3a, 5a, 7a, 9a and 12a and programmed to set the flows controlled by these valves so as to reduce the gap between the measured values and the set values.

In accordance with the invention, the cetane number of the mixture discharged by line 2 is also measured in line and the feeding flows of mixer 1 and injection flows of procetane into line 2 are adjusted so as to bring the measured cetane number of the desired set value closer to the. aforementioned number.

For this purpose, an apparatus 21 for measuring the ignition delay of the mixture being manufactured and that of the product with a known cetane number that is close to the set value, is fed:

on the one hand, a mixture to be tested, by a first line 22, connected to a loop circuit 23 for sample taking, shunt connected to line 2, downstream of the procetane injection;

on the other hand, a product with a known cetane number close to the set value of the desired creation, by a second line 24, from a tank 25.

Apparatus 21 is itself connected to a computer 14 and transmits a signal reflecting the difference between the measured known cetane number and the cetane number for the mixture, sample, in such a way that the flows of the various constituents can be adjusted accordingly by the computer.

Figure 2:
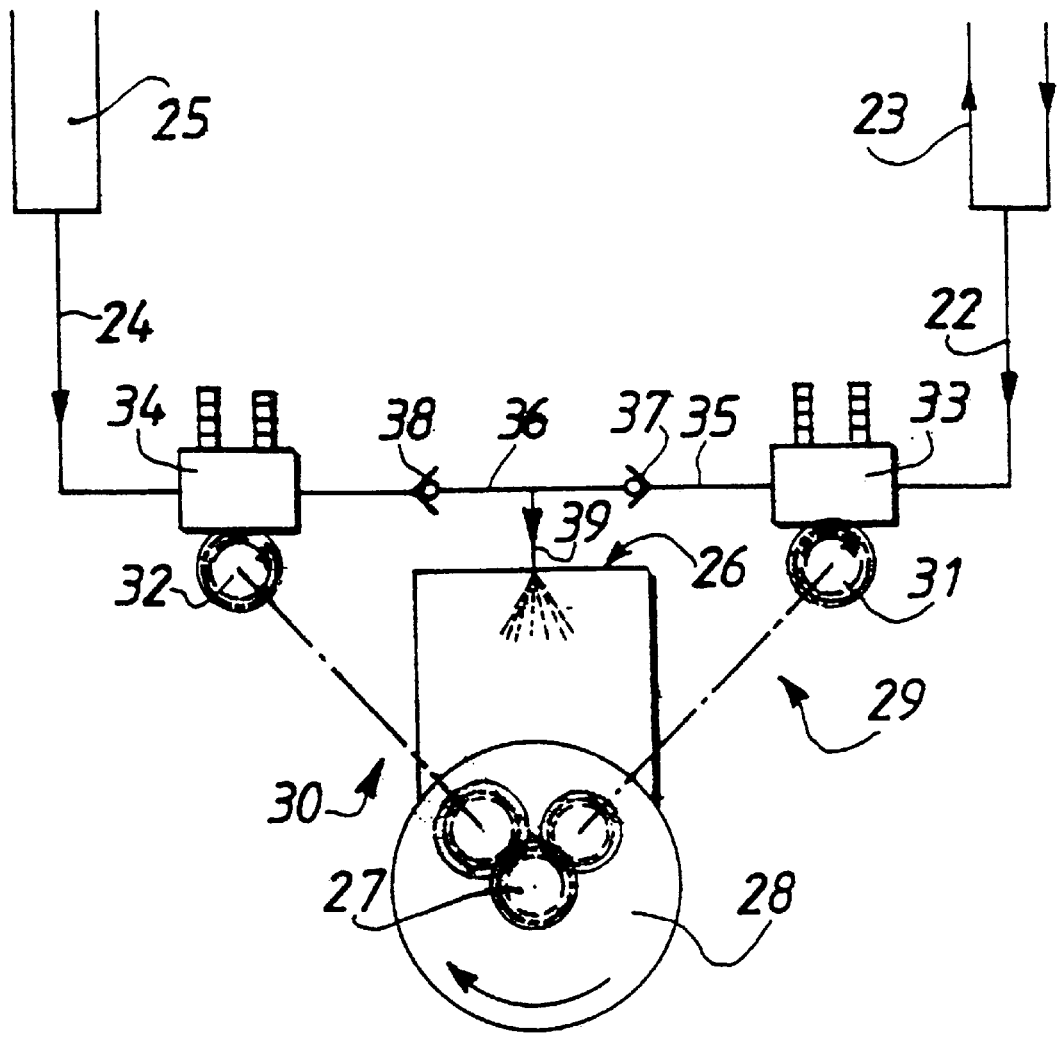
FIG. 2 shows the measuring system of the mixture's cetane number during fabrication.

Apparatus 21 is represented in detail in FIG. 2. It consists of a CFR type motor 26 operating at a constant compression ratio with a set advance, for example 13° in relation to the upper dead center (advance set by the ASTM D 613 standard). Motor 26 is command fed by lines 22 and 24 and results in a rotation of shaft 27, equipped with a flywheel 28. Shaft 27 is itself coupled, by transmission systems 29 and 30, for example with gears, to the two high pressure pumps 33 and 34, placed respectively on the feed line 22 of the mixture to be measured and on feed line 24 of the known cetane number product. These pumps are connected by lines, respectively 35 and 36, equipped with non-return valves, respectively 37 and 38, to an injection line 39, connected to the motor's injector.

As explained above, motor 26 is equipped with an automatic control system so as to feed the motor successively and periodically first with the mixture sample to be measured then with the known cetane number standard product.

The difference in motor response for these two products is converted by a calculation method into the difference between it and the cetane number, then transmitted in form of an electric signal to computer 14. The latter calculates the cetane number of the mixture sample by applying the rules of ASTM D 2885 standard, compares the obtained value with the set value determined for the mixture and adjusts the feed flows of the different constituents of the mixture or the injection of the procetane additive accordingly.

Only line 39, not very long, is common to both feeding circuits of motor 26, so that after one measurement it is not necessary to purge the circuit and the pump that were just used before completing the following measurement with the second circuit and the second pump. This is a considerable advantage in comparison with the ASTM D 613 method which uses one single pump and two standard products with known cetane numbers.

Therefore, for the first time, this invention offers a cetane number measurement system that can be used in line in a fuel preparation unit, in particular fuel for diesel motors, by mixing the. constituents of this fuel in line.

What is claimed is:

1. A method for preparing fuel for diesel motors or fuel for heating systems, by mixing constituents of said fuel in line optionally including additives, where the fuel has a specific cetane number, wherein the method comprises the steps of:

continuously feeding a mixer (1) with different constituents (3–9) at controlled flows (3a–9a), measuring, at the output of the mixer (1) and at different time intervals, the cetane number of the fuel being prepared, calculating the difference between the cetane number and at least one set value, and then adjusting the respective flows of the different constituents (3a–9a) or additives (12a) to eliminate the difference between the measured values and the set values, wherein a CFR type motor (26) operating at a constant compression ratio is alternately fed a fuel during manufacturing (22) from the exhaust line (2) of the mixer (1), and a standard product (25) with a known cetane number from a separate line, distinct from said exhaust line, and wherein both said exhaust line and said separate line have separate, individual high pressure injection pumps (33 and 34) allowing for the auto-ignition of the fuel.

2. The method according to claim 1, wherein that the time of the measurements on the fuel being manufactured then on the standard product is less than one hour.

3. The method according to claim 1, wherein that the ignition delay of a mixture sample during manufacturing and the ignition delay of a sample product with a known, cetane number are measured sequentially, under the same conditions and with the same CFR motor (26).

4. The method according to claim 1, wherein that the standard product used has a cetane number close to that sought for the mixture being manufactured, and for which the difference between it and the set value is less than 5 cetane points.

5. The method according to claim 1, wherein that the mixture sample and the standard product that feed the CFR motor are introduced through separate circuits or circuits that only have a small common portion in the same injection area of such motor.

6. The method according to claim 1, wherein that it further comprises an in line addition phase, in adjustable quantities, of a procetane additive, in the mixer, or either upstream or downstream of it.

7. The method according to claim 1, wherein the time of the measurements on the fuel being manufactured then on the standard product is less than 10 minutes.

8. The method according to claim 1, wherein the standard product used has a cetane number close to that sought for the mixture being manufactured, and for which the difference between it and the set value is less than 2.

9. An apparatus for the preparation of fuel for diesel motors or a fuel for heating systems, by in line mixing of constituents thereof and optionally additives, wherein said fuel must have a specific cetane number, wherein said apparatus comprises:

at least two tanks (4–10) for storage of at least two constitutents of the mixture, a mixer (1) fed various constituents of the mixture by at least two separate feed lines (3–9) with adjustable flows, at least one exhaust line (2) for the mixture prepared in mixer (1), a means of measuring a cetane number (21), and at least one means (14) of control for flow rates of the various feed lines (3–9) of said mixer (1) and a procetane feed line (12), wherein said means of control is controlled through comparisons and is programmed to adjust the different flow rates in order to reduce the gap between the measured values and set cetane number values, wherein the means of measurement designed to measure the mixture's cetane number consists of a CFR type motor (26) connected to an exhaust line for the mixture, the CFR motor (26) is connected by separate and distinct lines (22, 35; 24, 36) each individually equipped with a controlled means of closure, to said exhaust line and to a standard product source (25) with a known cetane number, the CFR motor (26) is pre-set at a predetermined value to separate at a constant compression ratio and with an advance to set injection, the CFR motor (26), through a means of control for the flow rate of the various feed lines for the constituents of the mixture, or optionally for the additives, can provide a signal that represents a difference between the two measurements of the cetane number, wherein measurements are taken successively from the mixture and from the standard product or vice versa.

10. The apparatus according to claim 9, wherein that the feed lines (22, 35; 24, 36) of the CFR motor (26) for the mixture sample to be tested and the product with the known cetane number are separate or only have a small portion in common.

11. The apparatus according to claim 9, wherein that the CFR motor's (26) feed lines (22, 35; 24, 36) for the mixture sample to be tested and the product with the known cetane number each include a high pressure injection pump.

12. The apparatus according to claim 9, wherein that the CFR motor's (26) feed lines (22, 35; 24, 36) for the mixture sample to be tested and the product with the known cetane number include a non-return valve (37, 38).

13. The apparatus according to claim 9, wherein that it includes a means for periodically controlling the feeding pumps (33, 34).

14. The apparatus according to claim 9, wherein that the CFR motor has been calibrated by at least two standards with cetane numbers close to the cetane number of the standard product.

15. The apparatus according to claim 9, further comprising a tank (20) for storing the prepared product.

16. The apparatus according to claim 9, further comprising a source of procetane additives (13) with an automated and adjustable flow, connected upstream or downstream of the mixer (1) and/or to the exhaust line (2).

17. The apparatus according to claim 9, wherein the means of measurement (21) designed to measure the mixture's cetane number consists of a CFR type motor (26) shunt connected to an exhaust line (2) of the mixture.

* * * * *